United States Patent [19]

Jenck

[11] 4,433,164

[45] Feb. 21, 1984

[54] ESTERS OF β,γ-UNSATURATED CARBOXYLIC ACIDS BY CARBONYLATION OF CONJUGATED DIENES

[75] Inventor: Jean Jenck, Villeurbanne, France

[73] Assignee: Rhone-Poulenc Industries, Paris, France

[21] Appl. No.: 341,101

[22] Filed: Jan. 20, 1982

[30] Foreign Application Priority Data

Jan. 23, 1981 [FR] France ................. 81 01205

[51] Int. Cl.$^3$ .............................................. C07C 67/38
[52] U.S. Cl. .................................. 560/207; 560/104; 560/114; 560/204; 260/410.9 R
[58] Field of Search ............... 560/207, 204, 104, 114; 260/410.9 R

[56] References Cited

U.S. PATENT DOCUMENTS

| | | | |
|---|---|---|---|
| 3,657,368 | 4/1972 | Parshall | 260/413 |
| 3,755,421 | 8/1973 | Fenton et al. | 560/207 |
| 3,778,466 | 12/1973 | Matsuda | 560/206 |
| 3,818,060 | 6/1974 | Forster | 260/413 |
| 3,821,265 | 6/1974 | Forster | 260/413 |
| 3,887,595 | 6/1975 | Nozaki | 560/204 |
| 3,968,133 | 7/1976 | Knifton | 260/413 |
| 3,991,101 | 11/1976 | Knifton | 560/207 |
| 4,172,087 | 10/1979 | Knifton | 560/207 |

FOREIGN PATENT DOCUMENTS 1080807 8/1967 United Kingdom .
1110405 4/1968 United Kingdom .
1123367 8/1968 United Kingdom .

OTHER PUBLICATIONS

Pearson, Ralph G., *Journal of Chemical Education*, vol. 45, (1968), pp. 581–587.
*The Condensed Chemical Dictionary*, (1974), 8th Ed., Van Nostrand, Publ. at p. 747.
Migrdichian, Vartkes Organic Synthesis, vol. 1, (1957), Reinhold, Publ. at p. 823.
Fieser & Fieser, *Organic Chemistry*, (1944), D. C. Heath, Publ. p. 229.

*Primary Examiner*—Natalie Trousof
*Assistant Examiner*—L. Hendriksen
*Attorney, Agent, or Firm*—Burns, Doane, Swecker & Mathis

[57] ABSTRACT

Esters of β,γ-unsaturated carboxylic acids, e.g., penten-3-oates, are prepared by carbonylating a necessarily conjugated diene, e.g., butadiene, with carbon monoxide, in the presence of (i) an alcohol corresponding to the desired ester, (ii) a halogen hydracid, (iii) a palladium catalyst which comprises palladium metal, a palladium oxide, or a salt of palladium, or ionic complex thereof, the anion coordinated with the palladium cation of which being a hard or intermediate base, and (iv) a quaternary onium salt of elemental nitrogen, phosphorus or arsenic, said elemental nitrogen, phosphorus or arsenic being tetracoordinated with carbon atoms and the anion of said salt comprising a hard or intermediate base.

24 Claims, No Drawings

ESTERS OF β,γ-UNSATURATED CARBOXYLIC ACIDS BY CARBONYLATION OF CONJUGATED DIENES

BACKGROUND OF THE INVENTION

1. Field of the Invention

The present invention relates to the preparation of esters of β,γ-unsaturated carboxylic acids via the carbonylation of dienes, and, more especially, via the carbonylation of conjugated dienes with carbon monoxide in the presence of alcohol.

2. Description of the Prior Art

It is known to this art, e.g., from Japanese Pat. No. 48-5564, to prepare esters of β,γ-unsaturated carboxylic acids by carbonylation of conjugated dienes with carbon monoxide in the presence of a monoalcohol, a halide-free palladium catalyst and a halogen hydracid, at a temperature on the order of 100° C. and under a carbon monoxide pressure on the order of 100 bars.

Unless a large amount of the catalyst and a high concentration of the halogen hydracid are used, this patented process does not simultaneously provide a high selectivity in the esters desired, a high conversion of the conjugated dienes and a good stability of the palladium catalyst.

It has also been proposed to prepare β,γ-unsaturated carboxylic acids or their esters by the carbonylation of conjugated dienes with carbon monoxide in an acid medium, in the presence of water or an alcohol, a palladium catalyst deposited upon suitable support and an organic phosphine. Compare French Pat. No. 1,461,826. This process displays the disadvantage of requiring high carbon monoxide pressures, for example, on the order of 700 bars.

U.S. Pat. No. 4,172,087 discloses the synthesis of penten-3-oic acid esters in admixture with a large amount of nonadien-3,8-oic acid esters, by the carbonylation of butadiene with carbon monoxide in the presence of an alcohol, an N-heterocyclic tertiary amine, and a palladium halide catalyst complexed with a monodentate tertiary phosphine, or a halide-free palladium salt complexed with a multidentate tertiary phosphine.

Such a process has very little selectivity as regards the esters penten-3-oic acid. Cf. U.S. Pat. No. 3,657,368.

SUMMARY OF THE INVENTION

Accordingly, a major object of the present invention is the provision of an improved process for the preparation of esters of β,γ-unsaturated carboxylic acids by the carbonylation of conjugated dienes, which process providing a high selectivity in the desired esters, improved conversions of the starting material conjugated dienes, together with good stability of the palladium catalyst, and with the temperatures and carbon monoxide pressures employed being on the same order of, or lower than those typically used in the carbonylation of conjugated dienes in the presence of palladium catalysts.

Briefly, the process according to the invention features the preparaion of esters of β,γ-unsaturated carboxylic acids, by carbonylation of a conjugated diene with carbon monoxide, in the presence of the alcohol corresponding to the desired ester, a halogen hydracid and a palladium catalyst, at a temperature ranging from 50° to 150° C. and under a carbon monoxide pressure ranging from 50 to 300 bars, and said process being characterized in that:

[i] the carbonylation is effected in the additional presence of a quaternary onium salt of an element of Group VB of the Periodic Table selected from among nitrogen, phosphorus and arsenic, said element being tetracoordinated with carbon atoms and said salt comprising an anion selected from among the "hard" or "intermediate" bases; and

[ii] the palladium catalyst comprises:
(1) palladium metal;
(2) a palladium oxide; or
(3) a palladium salt or ionic complex, the anion thereof, which is coordinated with the palladium cation, is also a "hard" or "intermediate" base.

The expressions "hard" or "intermediate" base as utilized herein denote those anions falling within the classic definition set forth by R. Pearson, at *J. Chem. Ed.*, 45, 581-7 (1968).

DETAILED DESCRIPTION OF THE INVENTION

More particularly according to this invention, the quaternary onium cations, the Group VB element of which is tetracoordinated with carbon atoms, are cations formed from nitrogen, phosphorus or arsenic and four monovalent hydrocarbon radicals which may be the same or different, the free valence of which is borne by a carbon atom, each such radical being directly bonded to the aforesaid Group VB element by said free valence, and further wherein any two of such radicals may together form a single divalent radical.

In a preferred embodiment of the process according to the invention, the quaternary onium salt comprises a quaternary onium cation having one of the following structural formulae (I), (II) or (III):

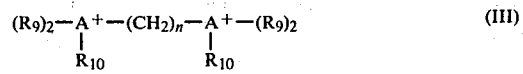

wherein A represents nitrogen, phosphorus or arsenic; $R_1$, $R_2$, $R_3$, $R_4$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms, and most preferably an alkenyl radical derived from the starting material conjugated diene; an aryl radical containing from 6 to 10 carbon atoms, optionally substituted by one or more alkyl substituents containing from 1 to 4 carbon atoms, or alkoxy, alkoxycarbonyl or halo substituents; and with the proviso that any two of said radicals $R_1$ to $R_4$ may together form a single linear or branched chain alkylene, alkenylene or alkadienylene radical containing from 3 to 6 carbon atoms; $R_5$, $R_6$, $R_7$, $R_8$, which also may be the same or different, are each a linear or branched chain alkyl radical containing from 1 to 4 carbon atoms; with the proviso that the $R_7$ and $R_8$ radicals may together form an alkylene radical containing from 3 to 6 carbon atoms; and with the further proviso that the $R_6$ and $R_7$ or $R_6$ and $R_8$ radicals may together form an alkylene, alkenylene or alkadienylene radical containing 4 carbon atoms and, together with the nitrogen atom, comprising a 5-membered nitrogen heterocycle; $R_9$ is a linear or branched chain alkyl radical containing from 1 to 4 carbon atoms, or a phenyl radical; $R_{10}$ is a linear or branched chain alkyl radical containing from 1 to 4 carbon atoms, and which may be the same or different from $R_9$; a linear or branched chain alkenyl radical containing from 2 to 12 carbon atoms, preferably from 4 to 8 carbon atoms, and more preferably an alkenyl radical derived from the starting material conjugated diene to be carbonylated; and n is an integer greater than or equal to 1 and less than or equal to 10, and preferably less than or equal to 6.

Representative of the "hard" or "intermediate" bases which may comprise the anion of said onium salts, the following ions are exemplary: $F^-$, $ClO_4^-$, $PF_6^-$, $BF_4^-$, $B\phi_4^-$, $PO_4^{3-}$, $HPO_4^{2-}$, $H_2PO_4^-$, $CH_3SO_3^-$,

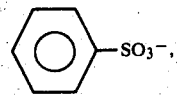

$HSO_4^-$, $NO_3^-$, $SO_4^{2-}$, $Cl^-$, $Br^-$, as well as those other anions within the definition of a "hard" or "intermediate" base per Pearson, supra.

For reasons of convenience of utilization, said anions are advantageously selected from among:

(i) $PO_4^{3-}$, $HPO_4^{2-}$, $H_2PO_4^-$, $CH_3SO_3^-$,

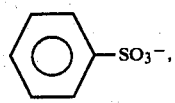

$NO_3^-$, $SO_4^{2-}$, $PF_6^-$, $Cl^-$, $Br^-$;
(ii) preferably from between $Cl^-$ and $Br^-$;
(iii) and more preferably is $Cl^-$.

Exemplary of the quaternary onium cations having the structural Formula (I), the following are representative:

(1) tetramethylammonium;
(2) triethylmethylammonium;
(3) tributylmethylammonium;
(4) trimethyl(n-propyl)ammonium;
(5) tetraethylammonium;
(6) tetrabutylammonium;
(7) dodecyltrimethylammonium;
(8) methyltrioctylammonium;
(9) heptyltributylammonium;
(10) tetrapropylammonium;
(11) tetrapentylammonium;
(12) tetrahexylammonium;
(13) tetraheptylammonium;
(14) tetraoctylammonium;
(15) tetradecylammonium;
(16) butyltripropylammonium;
(17) methyltributylammonium;
(18) pentyltributylammonium;
(19) methyldiethylpropylammonium;
(20) ethyldimethylpropylammonium;
(21) tetradodecylammonium;
(22) tetraoctadecylammonium;
(23) hexadecyltrimethylammonium;
(24) benzyltrimethylammonium;
(25) benzyldimethylpropylammonium;
(26) benzyldimethyloctylammonium;
(27) benzyltributylammonium;
(28) benzyltriethylammonium;
(29) phenyltrimethylammonium;
(30) benzyldimethyltetradecylammonium;
(31) benzyldimethylhexadecylammonium;
(32) dimethyldiphenylammonium;
(33) methyltriphenylammonium;
(34) buten-2-yltriethylammonium;
(35) N,N-dimethyl-tetramethyleneammonium;
(36) N,N-diethyl-tetramethyleneammonium;
(37) tetramethylphosphonium;
(38) tetrabutylphosphonium;
(39) ethyltrimethylphosphonium;
(40) trimethylpentylphosphonium;
(41) trimethylpentylphosphonium;
(42) octyltrimethylphosphonium;
(43) dodecyltrimethylphosphonium;
(44) trimethylphenylphosphonium;
(45) diethyldimethylphosphonium;
(46) dicyclohexyldimethylphosphonium;
(47) dimethyldiphenylphosphonium;
(48) cyclohexyltrimethylphosphonium;
(49) triethylmethylphosphonium;
(50) methyl-tri(isopropyl)phosphonium;
(51) methyl-tri(n-propyl)phosphonium;
(52) methyl-tri(n-butyl)phosphonium;
(53) methyl-tri(2-methylpropyl)phosphonium;
(54) methyltricyclohexylphosphonium;
(55) methyltriphenylphosphonium;
(56) methyltribenzylphosphonium;
(57) methyl-tri(4-methylphenyl)phosphonium
(58) methyltrixylylphosphonium;
(59) diethylmethylphenylphosphonium;
(60) dibenzylmethylphenylphosphonium;
(61) ethyltriphenylphosphonium;
(62) tetraethylphosphonium;
(63) ethyl-tri(n-propyl)phosphonium;
(64) triethylpentylphosphonium;
(65) hexadecyltributylphosphonium;
(66) ethyltriphenylphosphonium;
(67) n-butyl-tri(n-propyl)phosphonium;
(68) butyltriphenylphosphonium;
(69) benzyltriphenylphosphonium;
(70) ($\beta$-phenylethyl)dimethylphenylphosphonium;
(71) tetraphenylphosphonium;
(72) triphenyl(4-methylphenyl)phosphonium;
(73) tetrakis(hydroxymethyl)phosphonium;
(74) tetrakis(2-hydroxyethyl)phosphonium; and
(75) tetraphenylarsonium.

And exemplary of the Formula (II) cations are the following:

(1) N-methylpyridinium;
(2) N-ethylpyridinium;
(3) N-hexadecylpyridinium; and
(4) N-methylpicolinium.

Among the cations having the structural Formula (III), the following are representative:

(1) 1,3-bis(buten-2-yldimethylammonium)propane;

(2) 1,2-bis(trimethylammonium)ethane;
(3) 1,3-bis(trimethylammonium)propane;
(4) 1,4-bis(trimethylammonium)butane; and
(5) 1,3-bis(trimethylammonium)butane.

It may be advantageous, when the selected onium salt comprises a $Cl^-$ or $Br^-$ anion and a cation of Formula (I) or (III), wherein one of the radicals $R_1$ to $R_4$ or the radical $R_{10}$ is an alkenyl radical derived from the starting material conjugated diene, to prepare the onium salt "in situ" instead of preparing same prior to the carbonylation operation.

Indeed, it is especially easy to prepare this type of salt by the action of a tertiary amine, for example, on the product or products of the reaction of the conjugated diene with hydrochloric or hydrobromic acid.

Thus, when the conjugated diene to be carbonylated is 1,3-butadiene, it is envisaged to use as the quaternary onium salt, butenyl-alkylammonium chloride or bromide, which may be prepared "in situ" in the carbonylation reaction medium, by the action of a tertiary alkylamine on 1-chloro- or 1-bromo-2-butene, or on 3-chloro- or 3-bromo-1-butene; if the tertiary amine is, for example, triethylamine, it is possible to prepare in this manner "in situ" a butenyltriethylammonium chloride or bromide.

Among the palladium catalysts that may be used in one embodiment of the invention, the following are representative:

(1) palladium metal deposited on suitable support, such as charcoal, alumina, silica, and the like;

(2) the palladium oxides;

(3) salts or $\pi$-allylic complexes of palladium, the anion coordinated with the Pd being selected from among the following anions: carboxylates, such as formate, acetate, propionate, benzoate; $SO_4^{2-}$, $NO_3^-$, acetylacetonate, halides, such as $Cl-$ and $Br-$ and preferably $Cl-$;

(4) or zero palladium complexes comprising organic ligands not containing elements of Group VB, e.g., complexes such as bis(dibenzalacetone) Pd or bis(1,5-cyclooctadiene) Pd.

The process according to the invention is particularly adapted for the preparation of $\beta,\gamma$-unsaturated carboxylic esters from conjugated dienes comprising in their molecule the 1,3-butadiene skeleton and linear aliphaic monoalcohols containing from 1 to 3 carbon atoms, preferably 1 to 2 carbon atoms, and more preferably, ethanol.

Among such conjugated dienes comprising a 1,3-butadiene skeleton, the following are exemplary:

(i) linear or branched chain aliphatic dienes containing from 4 to 12 carbon atoms and preferably 4 to 8 carbon atoms, optionally substituted with inert substituents such as phenyl, cyclohexyl, nitro, oxo and particularly alkoxycarbonyl; and (ii) cyclic dienes containing 6 to 8 carbon atoms.

As specific examples of the conjugated dienes, exemplary are 1,3-butadiene, isoprene, piperylene, 1,3-hexadiene, 2,4-hexadiene, chloroprene, 1-cyclohexyl-1,3-butadiene, 1-phenyl-1,3-butadiene, 2,4-octadiene, 3-methyl-1,3-pentadiene, 2-methyl-2,4-pentadiene, 1,3-cyclohexadiene, 1,3-cyclooctadiene, optionally substituted with an alkoxycarbonyl group, such as methyl pentadien-2,4-oate.

The carbonylation consistent herewith is advantageously carried out in the presence of hydrochloric or hydrobromic acid, and particularly in the presence of HCl.

The hydrochloric acid may be introduced into the carbonylation medium in the gaseous form, or in the form of an organic compound capable of releasing hydrochloric acid in said medium, for example, in the form of 1-chloro-2-butene or 3-chloro-1-butene, in the case of the carbonylation of butadiene.

The immediately aforesaid has the considerable advantage of avoiding or reducing the secondary reactions of the alcohol employed, with the hydrochloric acid.

The respective amounts of the reactants to be used in the process according to the present invention may vary over very wide limits; it is self-evident that such amounts will be selected such that the process will be economically advantageous.

Thus, even though it is possible to use 0.5 to 10 times that amount of alcohol stoichiometrically required, it is preferable, in order to obtain maximum conversion of the conjugated diene, while avoiding excessive dilution of the medium with the alcohol, to carry out the process utilizing an alcohol/conjugated diene molar ratio ranging from about 0.8 to 5.

Similarly, the good activity of the subject palladium catalysts permits their use in very small amounts (corresponding to a molar ratio of the conjugated diene to palladium on the order of 2500) but the use of a large amount of the catalyst (corresponding to a conjugated diene/palladium molar ratio on the order of 100) is not harmful; the result desired being to effect a sufficiently rapid and selective carbonylation reaction, without excessive consumption of the catalyst, a conjugated diene/palladium ratio ranging from about 250 to 2000, and preferably ranging from about 250 to 1200 is generally preferable. It has been found that a molar ranging from about 500 and 700 is especially suitable to obtain a high conversion of conjugated dienes, particularly of butadiene, over a reasonable period of time, such that any degradation reactions are avoided.

The amount of the halogen hydracid to be used corresponds to a halogen hydracid/palladium ratio of at least 5. However, in order to avoid any change of the precipitation of palladium in the form of metal granules (precipitation due to a too low concentration of hydracid in the reaction medium), or of the degradation of alcohol into alkyl chlorides or dialkyl oxides (degradation due to an excessive concentration of hydracid medium), a halogen hydracid/palladium molar ratio ranging from 10 to 150, and preferably from 20 to 100, is advantageously selected. The selection of said ratio within these limits must also take into consideration the palladium concentration in the reaction medium; those skilled in this art fully appreciate that the higher the concentration of palladium in the reaction medium, the less high need be the hydracid/palladium ratio, and vice versa.

It too has been found that the beneficial effect provided by the presence, in the carbonylation reaction medium, of a quaternary onium salt as above-defined is notable when utilizing an onium cation/palladium ratio of 0.5; specifically, particularly advantageous results ensue when such ratio ranges from 1 to 15, with higher ratios not adversely affecting the carbonylation reaction.

In another embodiment of the subject carbonylation process, it is preferable that the choice of the onium cation/palladium ratio accounts for the palladium concentration in the reaction medium and particularly the conjugated diene/palladium molar ratio; thus, the higher the conjugated diene/palladium molar ratio, the more advantageous it is to employ higher onium cation/palladium ratio.

The elementary units corresponding to the term "moles" are the following:
(a) alcohol: gram molecule
(b) conjugated diene: gram molecule
(c) halogen hydracid: gram molecule
(d) palladium: gram atom
(e) quaternary onium cation: gram ion The carbonylation reaction is typically carried out at a temperature ranging from 50° to 150° C., preferably ranging from 80° to 130° C., and under a carbon monoxide pressure ranging from 50 to 250 bars.

The temperature and pressure are selected as functions of the activity and/or selectivity desired for a given catalyst, such as to obtain the best results possible. In effect, it is known that when the temperature decreases, the velocity of the diene conversion diminishes, but the selectivity as regards the desired monoester increases. It has also been found that when the carbon monoxide pressure is increased, the selectivity as regards the desired monoester is also increased.

The process according to the invention may be effected continuously or discontinuously; it has been found that an at least 70% rate of conversion of 1,3-butadiene may be obtained by carrying out the reaction discontinuously for 2 to 4 hours. The process displays but slight sensitivity to the presence of hydrogen or inert gases, such as nitrogen, argon or carbon dioxide, which may be present in addition to the carbon monoxide.

In order to further illustrate the present invention and the advantages thereof, the following specific examples are given, it being understood that same are intended only as illustrative and in nowise limitative.

In the examples to follow, the abbreviations set forth in the Tables I and X hereinafter connote the following definitions:
(i) Ex: Example;
(ii) BD: Butadiene;
(iii) EtOH: Ethanol;
(iv) Me: Methyl; Et: Ethyl; Oct: Octyl; $\phi$: Phenyl;
(v) Catalyst: Palladium catalyst;
(vi) [<(-PdCl]$_2$:bis[$\pi$-allyl palladium (II) chloride];
(vii) Cocatalyst: HCl or the product of the HCl+conjugated diene employed reaction;
(viii) Additive: Onium salt;
(ix) Pco: Carbon monoxide pressure.

The absence of the sign † signifies that the carbonylation reaction is carried out at constant pressure.

The presence of the sign † signifies that the carbonylation reaction is carried out at nonconstant pressure, commencing at 120 bars under cold conditions. Thus, † 157, for example, signifies that the carbon monoxide pressure is 120 bars in the cold state and is increased to 157 bars at the temperature of the carbonylation reaction, and subsequently declines as a function of the progress of the reaction.

EXAMPLES 1 TO 23

Preparation Of Ethyl Penten-3-oate; Use Of Different Onium Salts

General mode of operation:
Into a 125 cm3 autoclave fabricated from a nickel-molybdenum alloy of the trademark HASTELLOY B$_2$, the following materials were introduced under a stream of argon, in the amounts reported in Tables I and II:

(i) The catalyst in anhydrous state [palladium II chloride or bis[$\pi$-allyl palladium (II) chloride];

(ii) Absolute ethanol wherein gaseous hydrochloric acid had been solubilized, or to which 1-chloro-2-butene or 3-chloro-1-butene had been added; and (iii) An additive maintained in anhydrous state, corresponding or not corresponding to the quaternary onium salts, the use of which characterizing the present invention.

The autoclave was then closed; butadiene was subsequently charged therein in the amounts reported in Tables I and II.

Carbon monoxide was then introduced. Such introduction was carried out differently, depending on whether the carbonylation reaction was conducted at a constant or nonconstant pressure.

Carbonylation at constant CO pressure:
The autoclave, agitated by shaking, was heated to 120° C. while adding, at a constant pressure (145 bars, for example), gaseous commercial CO containing approximately 0.8% hydrogen by volume. The reaction was permitted to proceed for two hours at this temperature.

Carbonylation at nonconstant CO pressure:
Into the autoclave 120 bars of commercial CO were charged and the autoclave was heated to 120° C. The pressure was increased (for example, to 157 bars) in the autoclave. The reaction was permitted to proceed for 2 hours with a slow decline in the internal pressure (to 138 bars, for example).

After the two hours of carbonylation, at constant or varying pressure, as indicated in Tables I and II, the autoclave was cooled to 15° C. and slowly degassed. The reaction mass, having a lemon-yellow color, was analyzed by chromatography in the gaseous phase.

The formation of the following compounds was determined:

| | Abbreviation |
|---|---|
| (1) ethyl penten-3-oate | P$_3$ |
| (2) ethyl 2-methylbuten-3-oate | P' |
| (3) ethyl nonadien-3,8-oate | C$_9$ |
| (4) ethyl diesters having 6 carbon atoms (mainly diethyl 2-methylglutarate) | C$_6$ |
| (5) butadiene dimers (essentially 4-vinylcyclohexene) | HC$_8$ |
| (6) ethyl pentanoate | PA |
| (7) ethyl 2-methylbutanoate | |
| (8) 3-ethoxy-1-butene | ROC$_4$ |
| (9) 1-ethoxy-2-butene | |
| (10) ethyl penten-4-oate | P$_4$ |
| (11) 3-chloro-1-butene | ClC$_4$ |
| (12) 1-chloro-2-butene | |
| (13) ethyl chloride | Cl |
| (14) diethyl ether (extraneous reaction between HCl and ethanol) | |

Thus, in Example 12, beginning with:
(i) 75 mg (0.423 mmoles) of PdCl$_2$
(ii) 18 g (391 mmoles) ethanol
(iii) 770 mg (21.1 mmoles) HCl
(iv) 236 mg (0.85 mmoles) tetrabutylammonium chloride (v) 15 g (278 mmoles) butadiene
and two hours of carbonylation at 120° C., under a variable CO pressure of 158 bars, 34.7 g of a lemon-yellow reaction mass were obtained, the analysis of which by gas chromatography evidenced the following results:

| [I] | $P_3$ | 16.30 g | (127.3 mmoles) |
|---|---|---|---|
| [II] | P' | 0.56 g | (4.4 mmoles) |
| [III] | $C_9$ | 0.21 g | (1.15 mmoles) |
| [IV] | $C_6$ | 0.13 g | (0.6 mmoles) |
| [V] | $HC_8$ | 0.18 g | (1.65 mmoles) |
| [VI] | PA | traces | |
| [VII] | $ROC_4$ | 0.16 g | (1.6 mmoles) |
| [VIII] | $P_4$ | traces | |
| [IX] | $ClC_4$ | not calculated | |
| [X] | unconverted EtOH | 11.68 g | (253.9 mmoles) |
| [XI] | ethyl chloride + diethyl ether | 1.56 g | (24.2 mmoles) |
| [XII] | butadiene + traces of butene | 2.99 g | |

The abbreviations appearing in Tables I' and II' (and in III' to IX') connote the following definitions:

(i) TT: Total conversion of butadiene (in mole%)
(ii) RR: Partial conversion (in mole %) for each product obtained with respect to the butadiene charged, with $TT = \Sigma RR$.

Only the RR of the following products were taken into account for the calculations of TT: $P_3$, $P_4$, P', $C_9$, $C_6$, $HC_8$, PA and $ROC_4$; in fact, the chlorobutenes ($ClC_4$) were equivalent to a mixture of butadiene + carbonylable HCl in $P_3$.

(iii) RT: Selectivity (in mole %) for each product, with $RT = RR/TT$.
(iv) RRCl: Partial Conversion rate (in mole %) to ethyl chloride and diethyl ether, with respect to the ethanol charged.
(v) A: Activity of the catalyst expressed in number of moles of $P_3$ obtained per mole of Pd and per hour.

Analysis of results appearing in Tables I' and II':
[1] Examples 10 to 21 and 23 were carried out according to the present invention, utilizing the subject quaternary onium salts; the quaternary onium salts formed "in situ" in Examples 20 and 21, have the following formulae:

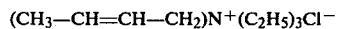

(CH$_3$—CH=CH—CH$_2$)N$^+$(C$_2$H$_5$)$_3$Cl$^-$ and

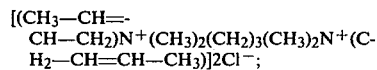

[(CH$_3$—CH=CH—CH$_2$)N$^+$(CH$_3$)$_2$(CH$_2$)$_3$(CH$_3$)$_2$N$^+$(CH$_2$—CH=CH—CH$_3$)]2Cl$^-$;

[2] Examples 1 and 22 were carried out without any additive; and
[3] Examples 2 to 9 were carried out in the presence of additives having formulae which did not correspond to those of the subject quaternary onium salts (either with respect to the cation, or to the anion).
It was determined that:

(a) The use of nonquaternary onium salts did not improve the selectivity in $P_3$, with respect to reaction carried out without any additive;
(b) The use of a quaternary onium salt, the anion of which was neither a hard nor an intermediate base was deleterious;
(c) The use of a quaternary onium salt according to the present invention resulted in marked improvement with respect to the parameters RT in $P_3$, TT and A, and this improvement increased with the size of the hydrocarbon radicals bonded to the element of Group VB of the Periodic Table.

EXAMPLES 24–27

Preparation Of Ethyl Penten-3-oate

Variation in the additive/Pd molar ratio:
Different carbonylation reactions were carried out for two hours consistent with the general mode of operation described hereinabove, at 120° C., in the presence of those amounts of those reagents reported in Table III, by varying the molar ratio of the tetrabutylammonium chloride to Pd from 0 to 10.

It was found (Table III') that under these conditions, the best results were obtained when said ratio was equal to 3, in particular concerning the activity A, which was multiplied by a factor of 2 in comparison with reaction conducted without additive.

EXAMPLES 28–36

Preparation Of Ethyl Penten-3-oate Variation In the HCl/Pd ratio:

Again consistent with the general mode of operation described hereinabove, different carbonylation reactions were carried out for two hours at 120° C., in the presence of those amounts of the reagents reported in Table IV, by varying the HCl/Pd ratio from 0 to 50.

It was found that (Table IV'):
(a) With a low or zero concentration in HCl, (Examples 29 and 31), the use of the subject additive resulted in scant improvement and did not prevent the precipitation of Pd° ($\downarrow$ Pd°);
(b) Under the conditions of the experiments, the presence of the subject additive enabled realization of stability of the palladium metal, with a molar ratio of HCl/Pd = 10, instead of 20 when the reaction was conducted in the absence of the additive.

EXAMPLES 37–41

Preparation Of Ethyl Penten-3-oate

Variation in the butadiene/Pd ratio:
Again following the general mode of operation described hereinabove, different carbonylation reactions were carried out for two hours at 120° C., in the presence of those amounts of those reagents reported in Table V, by varying the butadiene/Pd molar ratio.

It was found (Table V') that under these conditions:
(a) With a low Pd concentration (BD/Pd = 1200, approximately), best results were obtained with a NBu$_n$ $^+$Cl$^-$/Pd ratio of 6; a significant improvement in $P_3$ selectivity was determined;
(b) With an average concentration in Pd (BD/Pd = 500–600, approximately), best results were obtained with a NBu$_n$ $^+$Cl$^-$/Pd ratio of 3, wherein the activity A was multiplied by a factor of 2; and (c) With a high Pd concentration (BD/Pd=300, approximately), a very marked decrease in the amount of C9 formed was determined (practically non-existent).

EXAMPLES 42-46

Preparation Of Ethyl Penten-3-oate

Variation in the ethanol/butadiene ratio:

By following the general mode of operation described hereinabove, different carbonylation reactions were carried out for 2 hours at 120° C., in the presence of those amounts of those reagents reported in Table VI by varying the ethanol/butadiene molar ratio.

It was found (Table VI') that under these conditions:

(a) For an EtOH/DB ratio of about 1, the addition of a quaternary onium salt according to the invention gave rise to an increase in A;

(b) When said ratio was between 1.5 and 1.8, the addition of said onium salt increased, in addition to A, the selectivity in P3;

(c) When said ratio was about 4, the selectivity in P3 increased considerably.

EXAMPLES 47-50

Preparation Of Ethyl Penten-3-oate

Variation in the CO pressure:

By following the general mode of operation described hereinabove, different carbonylation reactions were carried out for 2 hours at 120° C., in the presence of those amounts of those reagents reported in Table VII and under the conditions of pressure reported in Table VII.

It was found (Table VII') that under the aforesaid conditions:

(a) The use of an additive in a NBu4 +Cl−/Pd ratio of 2 enabled a reduction in the carbon monoxide pressure from 155 bars to abut 120 bars, while the same activity, A, was maintained.

EXAMPLES 51-52

Preparation Of Ethyl Penten-3-oate

Variation in temperature:

By following the general mode of operation described hereinabove, different carbonylation reactions were carried out in the presence of those amounts of those reagents reported in Table VIII, at a pressure on the order of 135 to 155 bars and under the conditions of temperature reported in Table VIII.

It was found (Table VIII'):

(a) That at 120° C., even in the presence of a lesser amount of the palladium catalyst, the addition of NBu4 +Cl−, in a ratio of NBu4 +Cl−/Pd=3, effected a doubling in activity and an improved selectivity in P3; and (b) That at 100° C., the addition of a quaternary onium salt according to the invention increased the activity. It is thus economically advantageous to conduct the reaction at a slightly higher temperature to improve the selectivity in P3.

EXAMPLES 53-54

Preparation Of Methyl Penten-3-oate

By following the general mode of operation described hereinabove, the carbonylation of butadiene in the presence of methanol, in place of ethanol, was carried out, in the presence of those amounts of those reagents reported in Table IX and under the conditions of temperature and pressure reported in Table IX.

It was found that (Table IX'):

(a) Without any additive, the carbonylation reaction proceeded very slow, and the activity A and the selectivity in P3 were very weak, even when the proportion of the catalyst was very large; and (b) In the presence of an additive (NMeOCt3+Cl−), good activities A and selectivities in P3 were obtained.

EXAMPLES 55-56

Carbonylation Of Isoprene And Piperylene

By following the general mode of operation described hereinabove, the carbonylation of isoprene, on the one hand, and of piperylene on the other, were carried out, in the presence of ethanol, under the conditions reported in Table X.

The chromatographic analysis of the resultant solutions indicated the specific formation of the following products:

---

[I] Carbonylation of isoprene (i) Ethyl 4-methylpenten-3-oate 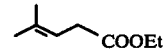

(ii) Ethyl 2,3-dimethylbuten-2-oate 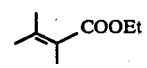

(iii) Ethoxypentenes + diethoxypentane (iv) Ethyl 5-ethoxy-4-methylpentanoate 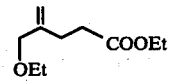

(v) Lactones

[II] Carbonylation of piperylene (i) Ethyl 2-methylpenten-3-oate 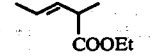

(ii) Ethoxypentenes
(iii) Piperylene dimers
(iv) Ethoxydecenes.

---

The results of these particular carbonylations are reported in Table X'.

EXAMPLE 57

Carbonylation Of Methyl Pentadien-2,4-oate

By following the general mode of operation described hereinabove, a carbonylation reaction was carried out in the presence of the following reagents in the following amounts thereof:

| | | |
|---|---|---|
| (i) Methyl pentadien-2,4-oate | 6.1 g | (54.4 mmoles) |
| (ii) Methanol | 3.48 g | (109 mmoles) |
| (iii) HCl | 350 mg | (9.6 mmoles) |
| (iv) PdCl2 | 21.4 mg | (0.12 mmoles) |
| (v) PBu4Cl | 180 mg | (0.61 mmoles) |

The reaction was carried out for 2 hours at 100° C. under a pressure of 180 bars; 10.3 g of a homogeneous solution of a lemon-yellow color were recovered.

The results of gas phase chromatographic analysis of the resultant solution were as follows:

[I] 4 g of carbonylation products (unsaturated diesters having 6 carbon atoms), consisting of:

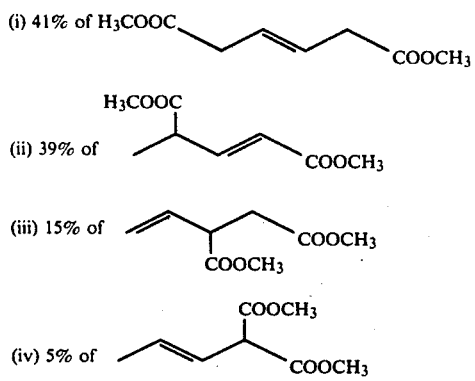

(i) 41% of H₃COOC-CH=CH-CH₂-COOCH₃

(ii) 39% of H₃COOC-CH(-)-CH=CH-COOCH₃ ... (structures shown)

(iii) 15% of CH₂=CH-CH(COOCH₃)-COOCH₃

(iv) 5% of ...-CH=CH-CH(COOCH₃)-COOCH₃

[II] 0.9 g dimers of methyl pentadien-2,4-oate.

The rate of partical conversion RR to unsaturated diesters was 43 mole %, which corresponded to a specific activity for all of the unsaturated diesters of 97 $h^{-1}$.

EXAMPLE 58

Preparation Of Ethyl Penten-3-oate

Use of a quaternary onium salt without the ambit of the invention:

By following the general mode of operation described hereinabove, a carbonylation reaction was carried out in the presence of the following reagents in the following amounts:

| | | |
|---|---|---|
| (i) Butadiene | 14.5 g | (268.5 mmoles) |
| (ii) Bis(π-allyl palladium chloride) | 0.077 g | (0.423 mmoles) |
| (iii) Ethanol | 18 g | (391.3 mmoles) |
| (iv) Crotyl chloride | 1.91 g | (21.15 mmoles) |
| (v) NEt₄ SnCl₃ | 0.3013 g | (0.846 mmole) |

The reaction was carried out for 2 hours at 120° C. under a variable carbon monoxide pressure of 150 bars.

21.8 g of a clear yellow solution were recovered, which contained precipitated palladium.

The results of the gas phase chromatographic analysis of the resultant solution was as follows:

| Products | Weight, g | mmoles | RT % | RR % |
|---|---|---|---|---|
| Ethoxybutene | 0.33 | 3.3 | 12.1 | 1.2 |
| Vinylcyclohexene | 0.30 | 5.6 | 20.6 | 2 |
| Ethyl 2-methylbuten-3-oate | 0.07 | 0.5 | 1.8 | 0.2 |
| P₃ | 2.28 | 17.8 | 65.4 | 6.6 |

The specific activity A was 21 $h^{-1}$ and the rate of conversion Tt of the butadiene was 10.1 mole %.

EXAMPLE 59

Preparation Of Ethyl Penten-3-oate

Use of a mixture of NEt₄ SnCl₃ and triphenylphosphine, without the scope of the invention:

By following the general mode of operation described hereinabove, a carbonylation reaction was carried out in the presence of the following reagents in the following amounts:

| | | |
|---|---|---|
| (i) Butadiene | 14 g | (259.2 mmoles) |
| (ii) Bis(π-allyl palladium chloride) | 0.0774 g | (0.423 mmole) |
| (iii) Ethanol | 18 g | (391.3 mmoles) |
| (iv) Gaseous HCl | 0.77 g | (21.1 mmoles) |
| (v) NEt₄ SnCl₃ | 0.3013 g | (0.846 mmole) |
| (vi) Triphenylphosphine | 0.1109 g | (0.423 mole) |

The reaction was carried out for 2 hours at 120° C. under a variable carbon monoxide pressure of 150 bars.

20.5 g of a clear, yellow solution containing precipitated palladium were recovered.

The results of the gas phase chromatographic analysis were as follows:

| Products | Weight, g | mmoles | RT % | RR % |
|---|---|---|---|---|
| Ethoxybutene | 0.28 | 2.8 | 13.7 | 1 |
| Vinylcyclohexene | 0.21 | 3.9 | 19 | 1.5 |
| Ethyl 2-methylbuten- | 0.05 | 0.4 | 2 | 0.1 |
| P₃ | 1.71 | 13.4 | 65.4 | 5.1 |

The specific activity A was 16 $h^{-1}$ and the rate of conversion TT of the butadiene was 7.9 mole %.

TABLE 1

| EX | BD mM | EtOH mM | Catalyst mM PdCl₂ | Cocatalyst mM HCl | BD/Pd molar ratio | HCl/Pd molar ratio | Additive | Additive/Pd molar ratio | PCO bars |
|---|---|---|---|---|---|---|---|---|---|
| 1 | 213 | 391 | 0.423 | 21.1 | 504 | 50 | — | 0 | ↑157 |
| 2 | 241 | 391 | 0.423 | 21.1 | 570 | 50 | NH₄⁺Cl⁻ | 2 | ↑153 |
| 3 | 250 | 391 | 0.423 | 21.1 | 592 | 50 | NEt₃ | 2 | ↑157 |
| 4 | 278 | 391 | 0.423 | 21.1 | 657 | 50 | Φ₃P=N⁺=PΦ₃Cl⁻ | 5 | ↑148 |
| *5 | 278 | 470 | 0.56 | 60 | 500 | 110 | PΦ₃ | 2 | ↑158 |
| 6 | 287 | 391 | 0.423 | 21.1 | 679 | 50 | N Bu₄⁺ I⁻ | 10 | ↑157 |
| 7 | 269 | 391 | 0.423 | 21.1 | 636 | 50 | N Bu₄⁺ SCN⁻ | 2 | 145 |
| 8 | 259 | 391 | 0.423 | 21.1 | 613 | 50 | Me PΦ₃⁺ I⁻ | 10 | ↑154 |
| 9 | 278 | 391 | 0.423 | 42.3 | 657 | 100 | Me PΦ₃⁺ I⁻ | 3 | ↑153 |
| 10 | 222 | 391 | 0.423 | 21.1 | 526 | 50 | N Me₄⁺ Cl⁻ | 2 | ↑157 |
| 11 | 250 | 391 | 0.423 | 21.1 | 592 | 50 | N Et₄⁺ Cl⁻ | 2 | ↑151 |
| 12 | 278 | 391 | 0.423 | 21.1 | 657 | 50 | N Bu₄⁺ Cl⁻ | 2 | ↑158 |
| 13 | 278 | 391 | 0.423 | 21.1 | 657 | 50 | N Me Oct₃⁺Cl⁻ | 2 | ↑158 |
| 14 | 241 | 391 | 0.423 | 21.1 | 570 | 50 | P Bu₄⁺Cl⁻ | 2 | ↑150 |
| 15 | 259 | 391 | 0.423 | 21.1 | 614 | 50 | AsΦ₄⁺Cl⁻ | 2 | ↑152 |

*Reaction for 3 hours, 20 minutes, instead of 2 hours

TABLE I'

| EX | Additive | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RR Cl % |
|---|---|---|---|---|---|---|---|---|---|---|---|---|---|---|---|---|
| 1 | — | 37.4 | 84 | 89.6 | 33.5 | 2.6 | 1 | 2.5 | 0.9 | 3.5 | 1.3 | 1.8 | 0.7 | ε | ε | 5.5 |
| 2 | $NH_4^+Cl^-$ | 41.2 | 104 | 88.8 | 36.6 | 3 | 1.2 | 2.7 | 1.1 | 3.5 | 1.4 | 1.7 | 0.7 | 0.2 | 0.1 | 6.4 |
| 3 | $NEt_3$ | 40.2 | 99 | 87 | 34.8 | 3.6 | 1.6 | 3.6 | 1.6 | 2.9 | 1.2 | ε | ε | 2.4 | 1 | 2.9 |
| 4 | $\Phi_3P=N^+=P\Phi_3Cl^-$ | 29.8 | 82 | 87.3 | 25.3 | 2.9 | 0.8 | 5 | 1.4 | 4.1 | 1.2 | ε | ε | 0.6 | 0.2 | 7.4 |
| 5 | $P\Phi_3$ | 11.8 | 5 | weak | | | | | | | | | | | | |
| 6 | $NBu_4^+I^-$ | 5.5 | 12 | 63.3 | 3.5 | ε | ε | ε | ε | 31.6 | 1.7 | 5 | 0.3 | ε | ε | 5.1 |
| 7 | $NBu_4^+SCN^-$ | 10 | 22 | 69 | 6.9 | 2.2 | 0.2 | ε | ε | 23.2 | 2.3 | 5.9 | 0.6 | ε | ε | 1 |
| 8 | $MeP\Phi_3^+I^-$ | 5.8 | 6 | 43.9 | 2.5 | ε | ε | 2.7 | 0.1 | 42.6 | 2.4 | 10.8 | 0.6 | 0.8 | 0.1 | 3.3 |
| 9 | $MeP\Phi_3^+I^-$ | 9.4 | 20 | 67.9 | 6.4 | ε | ε | ε | ε | 24 | 2.2 | 8 | 0.7 | ε | ε | 5.3 |
| 10 | $NMe_4^+Cl^-$ | 57.6 | 137 | 90.5 | 52.2 | 3.2 | 1.8 | 3.3 | 1.9 | 2.2 | 1.3 | ε | ε | 0.8 | 0.5 | 6 |
| 11 | $NEt_4^+Cl^-$ | 53.6 | 145 | 91.3 | 48.8 | 3 | 1.6 | 2.8 | 1.5 | 2.5 | 1.3 | ε | ε | 0.6 | 0.3 | 5.8 |
| 12 | $NBu_4^+Cl^-$ | 50.4 | 151 | 91.3 | 46 | 3.1 | 1.6 | 1.6 | 0.8 | 2.3 | 1.2 | 1.1 | 0.6 | 0.4 | 0.2 | 6.2 |
| 13 | $NMeOct_3^+Cl^-$ | 55.9 | 168 | 91.9 | 51.4 | 3.1 | 1.7 | 1.9 | 1.1 | 2.7 | 1.5 | ε | ε | 0.4 | 0.3 | 7.1 |
| 14 | $PBu_4^+Cl^-$ | 57.3 | 152 | 93.3 | 53.5 | 2.5 | 1.5 | 2.2 | 1.3 | 1 | 0.6 | ε | ε | 0.8 | 0.5 | 6 |
| 15 | $As\Phi_4^+Cl^-$ | 43.2 | 123 | 92.6 | 40 | 2.9 | 1.3 | 1.2 | 0.2 | 1.7 | 0.7 | 1.6 | 0.7 | ε | ε | 6 |

TABLE II

| EX | BD mM | EtOH mM | Catalyst $PdCl_2$ mM | Cocatalyst HCl mM | BD/Pd molar ratio | HCl/Pd molar ratio | Additive | Additive/Pd molar ratio | PCO bars |
|---|---|---|---|---|---|---|---|---|---|
| 16 | 287 | 391 | 0.423 | 21.1 | 679 | 50 | $NBu_4^+Br^-$ | 2 | ↑157 |
| 17 | 278 | 391 | 0.423 | 21.1 | 657 | 50 | $NBu_4^+PF_6^-$ | 2 | ↑156 |
| 18 | 250 | 391 | 0.423 | 21.1 | 592 | 50 | $NBu_4^+CH_3SO_3^-$ | 2 | 145 |
| 19 | 259 | 391 | 0.423 | 21.1 | 612 | 50 | $NBu_4^+H_2PO_4^-$ | 2 | 145 |

| EX | BD mM | EtOH mM | Catalyst mM | Cocatalyst HCl mM | BD/Pd molar ratio | HCl/Pd molar ratio | Additive | Additive/Pd molar ratio | PCO bars |
|---|---|---|---|---|---|---|---|---|---|
| 20 | 287 | 391 | 0.423 | 21.1 | 679 | 50 | $NEt_3$ | 2 | ↑157 |
| 21 | 260 | 391 | 0.423 | 21.1 | 613 | 50 | $Me_2N(CH_2)_3NMe_2$ | 2 | ↑157 |
| 22 | 250 | 391 | [<(—PdCl)]$_2$ 0.423/2 | 21.1 | 591 | 50 | — | — | 145 |
| 23 | 259 | 391 | 0.423/2 | 21.1 | 613 | 50 | $PBu_4^+Cl^-$ | 2 | 145 |

TABLE II'

| EX | Additive | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RT % | RR Cl % |
|---|---|---|---|---|---|---|---|---|---|---|---|---|---|---|---|---|
| 16 | $NBu_4^+Br^-$ | 48.7 | 147 | 89.9 | 43.7 | 3.2 | 1.6 | 3 | 1.5 | 3.7 | 1.8 | ε | ε | ε | ε | 5.2 |
| 17 | $NBu_4^+PF_6^-$ | 51 | 150 | 91.2 | 45.5 | 3.2 | 1.6 | 2.6 | 1.3 | 2.7 | 1.3 | ε | ε | 0.4 | 0.2 | 7 |
| 18 | $NBu_4^+CH_3SO_3^-$ | 56.7 | 152 | 90.5 | 51.3 | 3.1 | 1.8 | 2.3 | 1.3 | 2.9 | 1.7 | 0.3 | 0.2 | 0.8 | 0.4 | 2.4 |
| 19 | $NBu_4^+H_2PO_4^-$ | 61.4 | 171 | 90.9 | 55.8 | 3.4 | 2.1 | 2.4 | 1.5 | 1.9 | 1.2 | 0.1 | ε | 1.1 | 0.7 | 2.6 |
| 20 | $NEt_3$ + Cl$\diagdown$ | 50.6 | 156 | 90.9 | 46 | 3.1 | 1.6 | 2.1 | 1.1 | 2.8 | 1.4 | 0.3 | 0.2 | 0.7 | 0.4 | 2.1 |
| 21 | $Me_2N(CH_2)_3NMe_2$ + $\diagdown$Cl | 52 | 143 | 89.4 | 46.5 | 3 | 1.5 | 3.2 | 1.7 | 1.9 | 1 | 0.3 | 0.2 | 2 | 1 | 2.1 |
| 22 | — | 40.6 | 107 | 90.5 | 36.8 | 2.9 | 1.2 | 2.1 | 0.9 | 3.8 | 1.6 | 0.1 | ε | 0.4 | 0.2 | 2.3 |
| 23 | $PBu_4^+Cl^-$ | 58.3 | 164 | 91.7 | 53.4 | 3.2 | 1.9 | 2 | 1.1 | 2 | 1.1 | 0.2 | 0.1 | 0.9 | 0.5 | 1.8 |

TABLE III

| EX | BD mM | EtOH mM | $PdCl_2$ mM | HCL mM | BD/PD molar ratio | HCl/Pd molar ratio | $NBu_4^+Cl^-$/Pd molar ratio | PCO bars |
|---|---|---|---|---|---|---|---|---|
| 1 | 213 | 391 | 0.423 | 21.1 | 504 | 50 | 0 | ↑157 |
| 24 | 222 | 391 | 0.423 | 21.1 | 526 | 50 | 1 | ↑154 |
| 12 | 278 | 391 | 0.423 | 21.1 | 657 | 50 | 2 | ↑158 |
| 25 | 259 | 391 | 0.423 | 21.1 | 613 | 50 | 3 | 145 |
| 26 | 250 | 391 | 0.423 | 21.1 | 592 | 50 | 5 | ↑154 |
| 27 | 259 | 391 | 0.423 | 21.1 | 613 | 50 | 10 | ↑157 |

TABLE III'

| EX | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RRCl % |
|---|---|---|---|---|---|---|---|---|---|---|---|---|---|---|---|
| 1 | 37.4 | 84 | 89.6 | 33.5 | 2.6 | 1 | 2.5 | 0.9 | 3.5 | 1.3 | 1.8 | 0.7 | ε | ε | 5.5 |
| 24 | 50.7 | 121 | 91 | 46.1 | 3.3 | 1.7 | 3.1 | 1.6 | 2.1 | 1 | ε | ε | 0.5 | 0.3 | 6.2 |
| 12 | 50.4 | 151 | 91.3 | 46 | 3.1 | 1.6 | 1.6 | 0.8 | 2.3 | 1.2 | 1.1 | 0.6 | 0.4 | 0.2 | 6.2 |
| 25 | 55.3 | 156 | 91.8 | 50.9 | 2.5 | 1.4 | 1.8 | 1 | 1.3 | 0.7 | ε | ε | 1.5 | 0.8 | 3.7 |
| 26 | 48 | 128 | 90.8 | 43.7 | 2.8 | 1.4 | 3.8 | 1.8 | 2.6 | 1.2 | ε | ε | ε | ε | 6 |
| 27 | 49.6 | 129 | 86.5 | 42.8 | 2.6 | 1.3 | 6.8 | 3.4 | 3.3 | 1.6 | ε | ε | ε | ε | 8 |

TABLE IV

| EX | BD mM | EtOH mM | Catalyst mM | Cocatalyst mM HCl | BD/Pd molar ratio | HCl/Pd molar ratio | Additive | Additive/Pd molar ratio | PCO bars |
|---|---|---|---|---|---|---|---|---|---|
| | | | [<(—PdCl)$_2$ | | | | NBu$_4$$^+$Cl$^-$ | | |
| 28 | 241 | 391 | 0.423/2 | 0 | 569 | 0 | 0 | 0 | ↑157 |
| 29 | 241 | 391 | 0.423/2 | 0 | 569 | 0 | 2.11 | 5 | ↑152 |
| 30 | 222 | 391 | 0.423/2 | 1.35 | 526 | 3.2 | 0 | 0 | 145 |
| 31 | 222 | 391 | 0.423/2 | 1.35 | 526 | 3.2 | 2.11 | 5 | ↑157 |
| | | | PdCl$_2$ | | | | | | |
| 32 | 222 | 391 | 0.423 | 4.23 | 526 | 10 | 0 | 0 | ↑153 |
| 33 | 241 | 391 | 0.423 | 4.23 | 570 | 10 | 1.27 | 3 | 145 |
| 34 | 232 | 391 | 0.423 | 4.23 | 549 | 10 | 8.45 | 20 | 145 |
| 35 | 222 | 391 | 0.423 | 8.45 | 526 | 20 | 0 | 0 | ↑152 |
| 36 | 222 | 391 | 0.423 | 8.45 | 526 | 20 | 1.27 | 3 | 145 |
| 1 | 213 | 391 | 0.423 | 21.1 | 504 | 50 | 0 | 0 | ↑157 |
| 25 | 259 | 391 | 0.423 | 21.1 | 613 | 50 | 1.27 | 3 | 145 |

TABLE IV'

| EX | HCl/Pd molar ratio | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RR Cl % | ↓Pd° |
|---|---|---|---|---|---|---|---|---|---|---|---|---|---|---|---|---|---|
| 28 | 0 | 7.1 | 6.5 | 32.2 | 2.3 | 2.3 | 0.2 | 28.6 | 2 | 28 | 2 | 8.8 | 0.6 | ε | ε | ε | yes |
| 29 | 0 | 5.5 | 5 | 31.1 | 1.7 | ε | ε | 30.4 | 1.7 | 38.5 | 2.1 | ε | ε | ε | ε | ε | yes |
| 30 | 3.2 | 22.2 | 46 | 79.4 | 17.6 | 1.8 | 0.4 | 12 | 2.6 | 4.5 | 1 | 2.2 | 0.5 | ε | ε | 0.4 | yes |
| 31 | 3.2 | 26.7 | 56 | 80.4 | 21.5 | 2.8 | 0.8 | 13.1 | 3.5 | 3.7 | 1 | ε | ε | ε | ε | ε | yes |
| 32 | 10 | 19 | 35 | 70.2 | 13.4 | 1.4 | 0.2 | 13.1 | 2.5 | 10.8 | 2 | 4.5 | 0.8 | ε | ε | 0.3 | yes |
| 33 | 10 | 45.9 | 110 | 83.5 | 38.3 | 2.4 | 0.7 | 10.3 | 2.9 | 1.8 | 0.5 | 0.2 | ε | 1.6 | 0.5 | 1.2 | no |
| 34 | 10 | 47.9 | 108 | 82.3 | 39.4 | 1.8 | 0.9 | 11.9 | 5.7 | 2 | 1 | ε | ε | 1.4 | 0.7 | 1.1 | no |
| 35 | 20 | 33.5 | 76 | 86.3 | 28.9 | 2.1 | 0.7 | 5.5 | 1.9 | 4.4 | 1.5 | 1.6 | 0.5 | ε | ε | 2.2 | no |
| 36 | 20 | 53.9 | 130 | 92.6 | 49.5 | 0.3 | 0.1 | 4.1 | 2.2 | 1.4 | 0.8 | ε | ε | 0.9 | 0.5 | 1.9 | no |
| 1 | 50 | 37.4 | 84 | 89.6 | 33.5 | 2.6 | 1 | 2.5 | 0.9 | 3.5 | 1.3 | 1.8 | 0.7 | ε | ε | 5.5 | no |
| 25 | 50 | 55.3 | 156 | 91.8 | 50.9 | 2.5 | 1.4 | 1.8 | 1 | 1.3 | 0.7 | ε | ε | 1.5 | 0.8 | 3.7 | no |

TABLE V

| EX | BD mM | EtOH mM | PdCl$_2$ mM | HCl mM | BD/Pd molar ratio | HCl/Pd molar ratio | NBu$_4$$^+$Cl$^-$ mM | MBu$_4$$^+$Cl$^-$/Pd molar ratio | PCO bars |
|---|---|---|---|---|---|---|---|---|---|
| 37 | 204 | 391 | 0.212 | 10.6 | 960 | 50 | 0 | 0 | ↑151 |
| 38 | 259 | 391 | 0.212 | 10.6 | 1229 | 50 | 0.423 | 2 | 145 |
| 39 | 250 | 391 | 0.212 | 10.6 | 1184 | 50 | 1.266 | 6 | 145 |
| 1 | 213 | 391 | 0.423 | 21.1 | 504 | 50 | 0 | 0 | ↑157 |
| 24 | 222 | 391 | 0.423 | 21.1 | 526 | 50 | 0.42 | 1 | ↑154 |
| 25 | 259 | 391 | 0.423 | 21.1 | 613 | 50 | 1.27 | 3 | 145 |
| 27 | 259 | 391 | 0.423 | 21.1 | 613 | 50 | 4.2 | 10 | ↑157 |
| 40 | 222 | 391 | 0.845 | 42.3 | 263 | 50 | 0 | 0 | ↑154 |
| 41 | 250 | 391 | 0.845 | 42.3 | 296 | 50 | 1.69 | 2 | 145 |

TABLE V'

| EX | BD/Pd molar ratio | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RR Cl % |
|---|---|---|---|---|---|---|---|---|---|---|---|---|---|---|---|---|
| 37 | 960 | 22 | 80 | 77.4 | 17 | 1.8 | 0.4 | 4.9 | 1 | 8.3 | 1.8 | 7.6 | 1.7 | ε | ε | 2.4 |
| 38 | 1129 | 22 | 116 | 86.3 | 19 | 2.3 | 0.5 | 3.9 | 0.8 | 5.8 | 1.3 | 1.8 | 0.4 | ε | ε | 1.8 |
| 39 | 1184 | 29 | 150 | 87.6 | 25.4 | 2.5 | 0.7 | 5.2 | 1.5 | 3.9 | 1.1 | 0.7 | 0.2 | ε | ε | 2.5 |
| 1 | 504 | 37.4 | 84 | 89.6 | 33.5 | 2.6 | 1 | 2.5 | 0.9 | 3.5 | 1.3 | 1.8 | 0.7 | ε | ε | 5.5 |
| 24 | 526 | 50.7 | 121 | 91 | 46.1 | 3.3 | 1.7 | 3.1 | 1.6 | 2.1 | 1 | ε | ε | 0.5 | 0.3 | 6.2 |
| 25 | 613 | 55.3 | 156 | 91.8 | 50.9 | 2.5 | 1.4 | 1.8 | 1 | 1.3 | 0.7 | ε | ε | 1.5 | 0.8 | 3.7 |
| 27 | 613 | 49.6 | 129 | 86.4 | 42.8 | 2.6 | 1.3 | 6.8 | 3.4 | 3.3 | 1.6 | ε | ε | ε | ε | 8 |
| 40 | 263 | 66.3 | 80 | 92 | 61.1 | 2.9 | 1.9 | 0.9 | 0.6 | 2.7 | 1.8 | ε | ε | 1.5 | 1 | 22 |
| 41 | 296 | 41.8 | 58 | 93.7 | 39.2 | 2.2 | 0.9 | ε | ε | 1 | 0.4 | ε | ε | 0.9 | 0.4 | 5.3 |

TABLE VI

| EX | BD mM | EtOH mM | Catalyst mM | Cocatalyst mM | BD/Pd molar ratio | EtOH/Bd molar ratio | HCl/Pd molar ratio | Additive mM | Additive/Pd molar ratio | PCO bars |
|---|---|---|---|---|---|---|---|---|---|---|
|  |  |  | PdCl$_2$ | HCl |  |  |  | PBu$_4^+$Cl$^-$ |  |  |
| 42 | 269 | 261 | 0.423 | 21.1 | 636 | 0.97 | 50 | 0 | 0 | 145 |
| 43 | 278 | 261 | 0.423 | 21.1 | 658 | 0.94 | 50 | 0.423 | 1 | 145 |
|  |  |  |  |  |  |  |  | NBu$_4^+$Cl$^-$ |  |  |
| 35 | 222 | 391 | 0.423 | 8.45 | 526 | 1.76 | 20 | 0 | 0 | ↑152 |
| 36 | 222 | 391 | 0.423 | 8.45 | 526 | 1.76 | 20 | 1.27 | 3 | 145 |
| 1 | 213 | 391 | 0.423 | 21.1 | 504 | 1.84 | 50 | 0 | 0 | ↑157 |
| 25 | 259 | 391 | 0.423 | 21.1 | 613 | 1.51 | 50 | 1.27 | 3 | 145 |
| 44 | 185 | 800 | 0.34 | 6.8 | 544 | 4.3 | 20 | 0 | 0 | 145 |
| 45 | 194 | 800 | 0.34 | 6.8 | 570 | 4.1 | 20 | 1.02 | 3 | 145 |
| 46 | 185 | 800 | 0.34 | 6.8 | 544 | 4.3 | 20 | 4.1 | 12 | 145 |

TABLE VI'

| EX | EtOH/Bd molar ratio | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RR Cl % |
|---|---|---|---|---|---|---|---|---|---|---|---|---|---|---|---|---|
| 42 | 0.97 | 43.8 | 127 | 91.1 | 39.9 | 2.2 | 1 | 1.7 | 0.7 | 3 | 1.3 | 0.8 | 0.3 | 1.3 | 0.6 | 3 |
| 43 | 0.94 | 46.3 | 139 | 91.1 | 42.2 | 2.5 | 1.2 | 3 | 1.5 | 2.6 | 1.2 | 0.9 | 0.4 | ε | ε | 2.7 |
| 35 | 1.76 | 33.9 | 76 | 86.3 | 28.9 | 2.1 | 0.7 | 5.5 | 1.9 | 4.4 | 1.5 | 1.6 | 0.5 | ε | ε | 2.2 |
| 36 | 1.76 | 53.9 | 130 | 92.6 | 49.5 | 0.3 | 0.1 | 4.1 | 2.2 | 1.4 | ε | ε | ε | 0.9 | 0.5 | 1.9 |
| 1 | 1.84 | 37.4 | 84 | 89.6 | 33.5 | 2.6 | 1 | 2.5 | 0.9 | 3.5 | 1.3 | 1.8 | 0.7 | ε | ε | 5.5 |
| 25 | 1.51 | 55.3 | 156 | 91.8 | 50.9 | 2.5 | 1.4 | 1.8 | 1 | 1.3 | 0.7 | ε | ε | 1.5 | 0.8 | 3.7 |
| 44 | 4.3 | 24.3 | 47 | 71.7 | 17.4 | 1.3 | 0.3 | 18.9 | 4.6 | 4.9 | 1.2 | 3.1 | 0.7 | ε | ε | 0.9 |
| 45 | 4.1 | 21.9 | 49 | 77.8 | 17 | 2.3 | 0.5 | 13.7 | 3 | 4 | 0.9 | 2.1 | 0.5 | ε | ε | 0.7 |
| 46 | 4.3 | 27 | 63 | 85 | 23 | 2 | 0.5 | 9.6 | 2.6 | 2.2 | 0.6 | 1 | 0.3 | 0.2 | ε | 0.7 |

TABLE VII

| EX | BD mM | EtOH mM | PdCl$_2$ | HCl | BD/Pd molar ratio | HCl/Pd molar ratio | Additive | Additive/Pd molar ratio | PCO bars |
|---|---|---|---|---|---|---|---|---|---|
| 47 | 213 | 391 | 0.423 | 21.1 | 504 | 50 | 0 | 0 | ↑80 |
| 1 | 213 | 391 | 0.423 | 21.1 | 504 | 50 | 0 | 0 | 155 |
| 48 | 259 | 391 | 0.423 | 21.1 | 614 | 50 | NMe$_4^+$Cl$^-$ | 2 | ↑80 |
| 49 | 250 | 391 | 0.423 | 21.1 | 591 | 50 | NBu$^+$Cl$^-$ | 2 | 100 |
| 50 | 230 | 391 | 0.423 | 21.1 | 544 | 50 | NBu$_4^+$Cl$^-$ | 2 | 120 |
| 12 | 278 | 391 | 0.423 | 21.1 | 657 | 50 | NBu$_4^+$Cl$^-$ | 2 | ↑158 |

TABLE VII'

| EX | PCO bar | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RRCl % |
|---|---|---|---|---|---|---|---|---|---|---|---|---|---|---|---|---|
| 47 | 80 | 11.1 | 17 | 62.7 | 6.9 | 2 | 0.2 | 1.3 | 0.1 | 20.3 | 2.2 | 13.6 | 1.5 | ε | ε | 3.2 |
| 1 | 155 | 37.4 | 84 | 89.6 | 33.5 | 2.6 | 1 | 2.5 | 0.9 | 3.5 | 1.3 | 1.8 | 0.7 | ε | ε | 5.5 |
| 48 | 80 | 16.1 | 35 | 72.1 | 11.6 | 2.7 | 0.4 | 2.4 | 0.4 | 16.6 | 2.7 | 6.2 | 1 | ε | ε | 3 |
| 49 | 100 | 23.9 | 61 | 86.5 | 20.7 | 2.5 | 0.6 | 3.5 | 0.8 | 4.7 | 1.1 | 1.7 | 0.4 | 0.8 | 0.2 | 3.7 |
| 50 | 120 | 36.2 | 88 | 89.5 | 32.4 | 1.9 | 0.7 | 3.5 | 1.3 | 3.2 | 1.2 | 1.3 | 0.5 | 0.6 | 0.2 | 4 |
| 12 | 158 | 50.4 | 151 | 91.3 | 46 | 3.1 | 1.6 | 1.6 | 0.8 | 2.3 | 1.2 | 1.1 | 0.6 | 0.4 | 0.2 | 6.2 |

TABLE VIII

| EX | BD mM | EtOH mM | PdCl$_2$ mM | Cocatalyst | BD/Pd molar ratio | HCl/Pd molar ratio | NBu$_4^+$Cl$^-$/Pd molar ratio | T °C. | Duration h | PCO bars |
|---|---|---|---|---|---|---|---|---|---|---|
| 51 | 194 | 391 | 0.423 | HCl | 460 | 50 | 0 | 100 | 2 | ↑142 |
| 52 | 250 | 391 | 0.33 |  | 758 | 50 | 3 | 100 | 2 | 140 |
| 1 | 213 | 391 | 0.423 | HCl | 504 | 50 | 0 | 120 | 2 | ↑155 |
| 25 | 259 | 391 | 0.423 | HCl | 613 | 50 | 3 | 120 | 2 | 145 |

TABLE VIII'

| EX | T °C. | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RRCl % |
|---|---|---|---|---|---|---|---|---|---|---|---|---|---|---|---|---|
| 51 | 100 | 21.3 | 43 | 90.6 | 19.3 | 2.4 | 0.5 | 1.2 | 0.3 | 2.1 | 0.5 | 2.9 | 0.6 | 0.6 | 0.12 | 2.6 |

TABLE VIII'-continued

| EX | T °C. | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RRCl % |
|---|---|---|---|---|---|---|---|---|---|---|---|---|---|---|---|---|
| 52 | 100 | 20.6 | 70 | 90.1 | 18.6 | 2.5 | 0.5 | 2.3 | 0.5 | 2.9 | 0.6 | 1.6 | 0.3 | ε | ε | 0.9 |
| 1 | 120 | 37.4 | 84 | 89.6 | 33.5 | 2.6 | 1 | 2.5 | 0.9 | 3.5 | 1.3 | 1.8 | 0.7 | ε | ε | 5.5 |
| 25 | 120 | 55.3 | 156 | 91.8 | 50.9 | 2.5 | 1.4 | 1.8 | 1 | 1.3 | 0.7 | ε | ε | 1.5 | 0.8 | 3.7 |

TABLE IX

| EX | BD mM | CH3OH mM | PdCl2 mM | Cl mM | BD/Pd molar ratio | HCl/Pd molar ratio | NMeOct3+Cl−/Pd molar ratio | T °C. | Duration h | PCO bars |
|---|---|---|---|---|---|---|---|---|---|---|
| 53 | 1340 | 3290 | 2.7 | 320 | 500 | 118 | 0 | 120 | 22 | 145 |
| 54 | 278 | 391 | 0.423 | 21.1 | 657 | 50 | 2 | 120 | 2 | 145 |

TABLE IX'

| EX | TT % | A | P3 RT % | P3 RR % | P' RT % | P' RR % | C9 RT % | C9 RR % | HC8 RT % | HC8 RR % | ROC4 RT % | ROC4 RR % | C6 RT % | C6 RR % | RRCl % |
|---|---|---|---|---|---|---|---|---|---|---|---|---|---|---|---|
| 53 | 6 | 1.5 | weak | | | | | | | | | | | | |
| 54 | 16.8 | 34 | 61.3 | 10.3 | 1.7 | 0.3 | 17.7 | 3 | 13 | 2.2 | 6.2 | 1 | | | |

TABLE X

| EX | diene | mM diene | EtOH mM | PdCl2 mM | HCl mM | BD/Pd molar ratio | HCl/Pd molar ratio | NBu4+Cl−/Pd molar ratio | t°C. | Duration h | PCO bars |
|---|---|---|---|---|---|---|---|---|---|---|---|
| 55 |  | 278 | 39 | 0.423 | 21.1 | 658 | 50 | 2 | 120 | 2 | 145 |
| 56 |  | 93 | 130 | 0.141 | 7 | 658 | 50 | 2 | 120 | 2 | 145 |

TABLE X'

| EX | TT % | A | 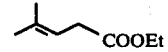COOEt RT % | RR % | 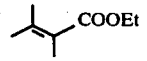COOEt RT % | RR % | Ethoxy pentenes RT % | RR % | Ethoxy decenes RT % | RR % | Lactones RT % | RR % | RR Cl % |
|---|---|---|---|---|---|---|---|---|---|---|---|---|---|
| 55 | 78.5 | 218 | 84.5 | 66.3 | 4.9 | 3.9 | 4 | 3.1 | 5.9 | 4.8 | 1.8 | 1.4 | 1.1 |

| EX |  RT % | RR % | Ethoxy pentenes RT % | RR % | Ethoxy decenes RT % | RR % | Dimers RT % | RR % | |
|---|---|---|---|---|---|---|---|---|---|
| 56 | 37 | 26 | 20.8 | 7.7 | 65 | 24 | 0.9 | 0.3 | 1.4 | 0.5 | 3.1 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an ester of a β,γ-unsaturated carboxylic acid, comprising carbonylating a conjugated diene with carbon monoxide, at a temperature ranging from about 50° to 150° C. under a carbon monoxide pressure ranging from about 50 to 300 bars, and in the presence of (i) an alcohol corresponding to the desired ester, (ii) a halogen hydracid, (iii) a palladium catalyst which comprises palladium metal, a palladium oxide, or a salt of palladium, or ionic complex thereof, the anion coordinated with the palladium cation of which being a hard or intermediate base, the ratio of halogen hydracid to palladium being at least 5, and (iv) a quaternary onium salt of nitrogen, phosphorus or arsenic, said nitrogen, phosphorus or arsenic being tetracoordinated with carbon atoms and the anion of said salt comprising a hard or intermediate base.

2. The process as defined by claim 1, wherein said quaternary onium salt (iv) the nitrogen, phosphorus or arsenic is tetracoordinated with four monovalent hydrocarbon radicals, the free valences of which being borne by carbon atoms.

3. The process as defined by claim 1, the cation of said quaternary onium salt (iv) having one of the following structural formulae (I), (II) or (III):

$$R_1-\overset{R_3}{\underset{R_2}{A^+}}-R_4 \qquad (I)$$

$$R_5-\overset{R_6}{\underset{}{N^+}}=C\overset{R_7}{\underset{R_8}{\diagdown}} \qquad (II)$$

-continued

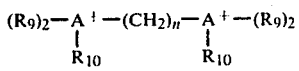

wherein A represents nitrogen, phosphorus or arsenic; $R_1$, $R_2$, $R_3$, $R_4$, which may be the same or different, are each a linear or branched chain alkyl radical containing from 1 to 16 carbon atoms, or such alkyl radical substituted with a phenyl, hydroxy, halo, nitro, alkoxy or alkoxycarbonyl substituent; a linear or branched chain alkenyl radical containing from 2 to 12 carbon atoms; an aryl radical containing from 6 to 10 carbon atoms, or such radical substituted by one or more alkyl substituents containing from 1 to 4 carbon atoms, or alkoxy, alkoxycarbonyl or halo substituents; and with the proviso that any two of said radicals, $R_1$ to $R_4$ may together form a single linear or branched chain alkylene, alkenylene or alkadienylene radical containing from 3 to 6 carbon atoms; $R_5$, $R_6$, $R_7$, $R_8$, which also may be the same or different, are each a linear or branched chain alkyl radical containing from 1 to 4 carbon atoms; with the proviso that the $R_7$ and $R_8$ radicals may together form an alkylene radical containing from 3 to 6 carbon atoms; and with the further proviso that the $R_6$ and $R_7$ or $R_6$ and $R_8$ radicals may together from an alkylene, alkenylene or alkadienylene radical containing 4 carbon atoms and, together with the nitrogen atom, comprising a 5-membered nitrogen heterocycle; $R_9$ is a linear or branched chain alkyl radical containing from 1 to 4 carbon atoms, or a phenyl radical; $R_{10}$ is a linear or branched chain alkyl radical containing from 1 to 4 carbon atoms, and which may be the same or different from $R_9$; or a linear or branched chain alkenyl radical containing from 2 to 12 carbon atoms; and n is a number ranging from 1 to 10.

4. The process as defined by claim 3, wherein $R_2$ and $R_{10}$ are each a linear or branched chain alkenyl radical containing from 4 to 8 carbon atoms.

5. The process as defined by claim 3, wherein $R_2$ and $R_{10}$ are each an alkenyl radical derived from the starting material conjugated diene.

6. The process as defined by claim 3, wherein n ranges from 1 to 6.

7. The process as defined by claim 3, the anion of said quaternary onium salt (iv) comprising $F^-$, $ClO_4^-$, $B\phi_4^-$, $PO_4^{3-}$, $HPO_4^{2-}$, $H_2PO_4^-$, $CH_3SO_3^-$,

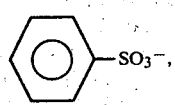

$HSO_4^-$, $NO_3^-$, $SO_4^{2-}$, $Cl^-$ or $Br^-$.

8. The process as defined by claim 7, the cation of said quaternary onium salt (iv) comprising tetramethylammonium; triethylmethylammonium; tributylmethylammonium; trimethyl(n-propyl)ammonium; tetraethylammonium; tetrabutylammonium; dodecyltrimethylammonium; methyltrioctylammonium; heptyltributylammonium; tetrapropylammonium; tetrapentylammonium; tetrahexylammonium; tetraheptylammonium; tetraoctylammonium; tetradecylammonium; butyltripropylammonium; methyltributylammonium; pentyltributylammonium; methyldiethylpropylammonium; ethyldimethylpropylammonium; tetradodecylammonium; tetraoctadecylammonium; hexadecyltrimethylammonium; benzyltrimethylammonium; benzyldimethylpropylammonium; benzyldimethyloctylammonium; benzyltributylammonium; benzyltriethylammonium; phenyltrimethylammonium; benzyldimethyltetradecylammonium; benzyldimethylhexadecylammonium; dimethyldiphenylammonium; methyltriphenylammonium; buten-2-yltriethylammonium; N,N-dimethyl-tetramethyleneammonium; N,N-diethyl-tetramethyleneammonium; tetramethylphosphonium; tetrabutylphosphonium; ethyltrimethylphosphonium; trimethylpentylphosphonium; trimethylpentylphosphonium; octyltrimethylphosphonium; dodecyltrimethylphosphonium; trimethylphenylphosphonium; diethyldimethylphosphonium; dicyclohexyldimethylphosphonium; dimethyldiphenylphosphonium; cyclohexyltrimethylphosphonium; triethylmethylphosphonium; methyl-tri(isopropyl)phosphonium; methyl-tri(n-propyl)phosphonium; methyl-tri(n-butyl)phosphonium; methyl-tri(2-methylpropyl)phosphonium; methyltricyclohexylphosphonium; methyltriphenylphosphonium; methyltribenzylphosphonium; methyl-tri(4-methylphenyl)phosphonium; methyltrixylylphosphonium; diethylmethylphenylphosphonium; dibenzylmethylphenylphosphonium; ethyltriphenylphosphonium; tetraethylphosphonium; ethyl-tri(n-propyl)phosphonium; triethylpentylphosphonium; hexadecyltributylphosphonium; ethyltriphenylphosphonium; n-butyl-tri(n-propyl)phosphonium; butyltriphenylphosphonium; benzyltriphenylphosphonium; ($\beta$-phenylethyl)dimethylphenylphosphonium; tetraphenylphosphonium; triphenyl(4-methylphenyl)phosphonium; tetrakis(hydroxymethyl)phosphonium; tetrakis(2-hydroxyethyl)phosphonium; tetraphenylarsonium; N-methylpyridinium; N-ethylpyridinium; N-hexadecylpyridinium; N-methylpicolinium; 1,3-bis(buten-2-yldimethylammonium)propane; 1,2-bis(trimethylammonium)ethane; 1,3-bis(trimethylammonium)propane; 1,4-bis(trimethylammonium)butane; or 1,3-bis(trimethylammonium)butane.

9. The process as defined by claim 3, said palladium catalyst (iii) comprising supported palladium metal.

10. The process as defined in claim 3, said palladium catalyst (iii) comprising an oxide of palladium.

11. The process as defined by claim 3, said palladium catalyst (iii) comprising a salt or $\pi$-allylic complex of palladium, the anion coordinated with the Pd being carboxylate, $SO_4^{2-}$, $NO_3^-$, acetylacetonate or halide.

12. The process as defined by claim 3, said palladium catalyst (iii) comprising a zero palladium complex of an organic ligand devoid of element of Group VB of the Periodic Table.

13. The process as defined by claim 3, the starting material conjugated diene being 1,3-butadiene, isoprene, piperylene, 1,3-hexadiene, 2,4-hexadiene, chloroprene, 1-cyclohexyl-1,3-butadiene, 1-phenyl-1,3-butadiene, 2,4-octadiene, 3-methyl-1,3-pentadiene, 2-methyl-2,4-pentadiene, 1,3-cyclohexadiene, 1,3-cyclooctadiene or methyl pentadien-2,4-oate.

14. The process as defined by claim 3, said carbonylation reaction being carried out utilizing the following molar ratios of the following materials:
  alcohol/conjugated diene: 0.5 to 10;
  conjugated diene/palladium: 100 to 2500;
  halogen hydracid/palladium: at least 5;
  onium cation/palladium: at least 0.5.

15. The process as defined by claim 14, said molar ratios/materials being as follows:
  alcohol/conjugated diene: 0.8 to 5;
  conjugated diene/palladium: 250 to 1200;

halogen hydracid/palladium: 10 to 150;
onium cation/palladium: 1 to 15.

16. The process as defined by claim 15, said halogen hydracid/palladium molar ratio ranging from 20 to 100.

17. The process as defined by claim 1, for the preparation of ethyl penten-3-oate, said conjugated diene being butadiene, said alcohol being ethanol, said halogen hydracid being hydrochloric acid, said palladium catalyst being palladium II chloride or bis[$\pi$-allyl palladium (II) chloride], and said carbonylation reaction being carried out utilizing the following molar ratios of the following materials:
ethanol/butadiene: 1 to 5;
butadiene/palladium: 250 to 1200;
HCl/palladium: 10 to 150;
onium cation/palladium: 1 to 15.

18. The process as defined by claim 17, said butadiene/palladium molar ratio ranging from 500 to 700, and said halogen hydracid/palladium molar ratio ranging from 20 to 100.

19. The process as defined by claim 3, the cation of said quaternary onium salt (iv) having the structural formula (I).

20. The process as defined by claim 3, the cation of said quaternary onium salt (iv) having the structural formula (II).

21. The process as defined by claim 3, the cation of said quaternary onium salt (iv) having the structural formula (III).

22. The process as defined by claims 19 or 21, wherein A is nitrogen.

23. The process as defined by claims 19 or 21, wherein A is phosphorus.

24. The process as defined by claims 19 or 21, wherein A is arsenic.

* * * * *